(12) United States Patent
Antonelli et al.

(10) Patent No.: US 7,011,683 B2
(45) Date of Patent: Mar. 14, 2006

(54) ATTACHMENT MECHANISM FOR MIDDLE EAR PROSTHESIS

(76) Inventors: Patrick Antonelli, c/o University of Florida, 1600 SW. Archer Rd., Suite M228, Gainesville, FL (US) 32610-0264; Anthony D. Prescott, c/o Grace Medical, Inc., 7731 Highway 70, Suite 107, Bartlett, TN (US) 38133

( * ) Notice: Subject to any disclaimer, the term of this patent is extended or adjusted under 35 U.S.C. 154(b) by 105 days.

(21) Appl. No.: 10/814,463

(22) Filed: Mar. 31, 2004

(65) Prior Publication Data
US 2004/0181281 A1 Sep. 16, 2004

Related U.S. Application Data

(62) Division of application No. 10/041,324, filed on Jan. 8, 2002, now Pat. No. 6,726,719.

(51) Int. Cl.
*A61F 2/18* (2006.01)
(52) U.S. Cl. ............................. 623/10; 600/25; 607/55

(58) Field of Classification Search ................. 623/10; 600/25; 607/55, 137
See application file for complete search history.

(56) References Cited

U.S. PATENT DOCUMENTS

| 4,130,905 A | 12/1978 | Mercandino |
| 4,655,776 A | 4/1987 | Lesinski |
| 4,728,327 A | 3/1988 | Gersdorff |
| 5,935,167 A | 8/1999 | a Wengen |
| 6,168,625 B1 | 1/2001 | Prescott |
| 6,197,060 B1 | 3/2001 | Knox |
| 6,203,571 B1 | 3/2001 | Magnan et al. |

*Primary Examiner*—David J. Isabella
(74) *Attorney, Agent, or Firm*—Wood, Phillips, Katz, Clark & Mortimer (57) ABSTRACT

A middle ear prosthesis comprises a piston adapted to extend through an oval window when implanted in a human ear. A pair of jaws engage an ossicle when implanted in a human ear. A spring is coupled to the jaws for biasing the jaws toward one another to provide clamping pressure. The jaws are in turn connected to the piston.

14 Claims, 9 Drawing Sheets

ATTACHMENT MECHANISM FOR MIDDLE EAR PROSTHESIS

This application is a division of 10/041,324, filed Jan. 8, 2002, now U.S. Pat. No. 6,726,719.

FIELD OF THE INVENTION

This invention relates to an ossicular prosthesis used for replacement and reconstruction and, more particularly, to an attachment mechanism for an ossicular prosthesis.

BACKGROUND OF THE INVENTION

Due to disease, trauma or congenital malformation, the ossicles of the middle ear are sometimes damaged. One common cause is otosclerosis.

The human ear includes three parts, identified generally as the outer ear, the middle ear and the inner ear. The middle ear includes three small bones. The malleus, or hammer, connects to the tympanic membrane, also known as the eardrum, of the outer ear. The malleus is in turn connected to the incus, or anvil. The incus is connected to the stapes, or stirrup. These three small bones are also commonly referred to ossicles or collectively the ossicular chain. The three bones operate as a lever system which amplify force of sound vibrations. The stapes is in turn connected to the oval window of the inner ear. The stapes applies pressure at the oval window which is transmitted to parts of the cochlea of the inner ear. A disease such as otosclerosis can result in fixation of the stapes. This can lessen or eliminate vibration of the stapes resulting in a conductive hearing loss.

One known treatment of otosclerosis and other damage to the stapes is treatment by surgery which replaces the stapes with a prosthesis. The stapes bone is typically reconstructed by creating an opening into the oval window by removal of a portion or all of the damaged stapes. The stapes prosthesis is placed into the newly created opening. The prosthesis is attached to a remaining middle ear ossicle, referred to as the anchoring ossicle, so that sound vibrations are transmitted from the ear drum to the oval window opening.

A typical stapes prosthesis consists primarily of two components. The first is a cylindrical portion, often referred to as a piston, designed to fit into the oval window opening. An attachment mechanism which may be a wire bent into the shape of a shepherd's hook, a plastic doughnut shaped member, or a cup, is attached to the cylindrical portion and is designed to be crimped or closed around the anchoring ossicle. Such attachment mechanisms are typically difficult to close properly around the anchoring ossicle. The opportunity for physicians to practice the closure technique is limited. If the attachment mechanism is closed improperly, the prosthesis will be either too loose, resulting in a poor hearing result, or too tight, resulting in destruction of the ossicle to which it is attached. Some stapes prosthesis consist of a plastic loop which require the surgeon to open the loop prior to insertion which causes permanent plastic deformation. After implantation, the surgeon must still close the device to ensure firm attachment. The axis of the long process of the incus is seldom perpendicular to the central axis of the oval window opening. As a result, any improper alignment can render the prosthesis prone to loosening. Additionally, known prosthesis devices may be difficult to remove if revision is desired.

The present invention is directed to improvements in attachment mechanisms for middle ear prosthesis.

SUMMARY OF THE INVENTION

In accordance with the invention, there is disclosed an attachment mechanism for a middle ear prosthesis.

Broadly, there is disclosed herein a middle ear prosthesis comprising a piston adapted to extend through an oval window when implanted in a human ear. A pair of jaws engage an ossicle when implanted in a human ear. A spring is coupled to the jaws for biasing the jaws toward one another to provide clamping pressure. Means are provided for operably connecting the jaws to the piston.

Further features and advantages of the invention will be readily apparent from the specification and from the drawings.

DETAILED DESCRIPTION OF THE INVENTION

Figure 1:
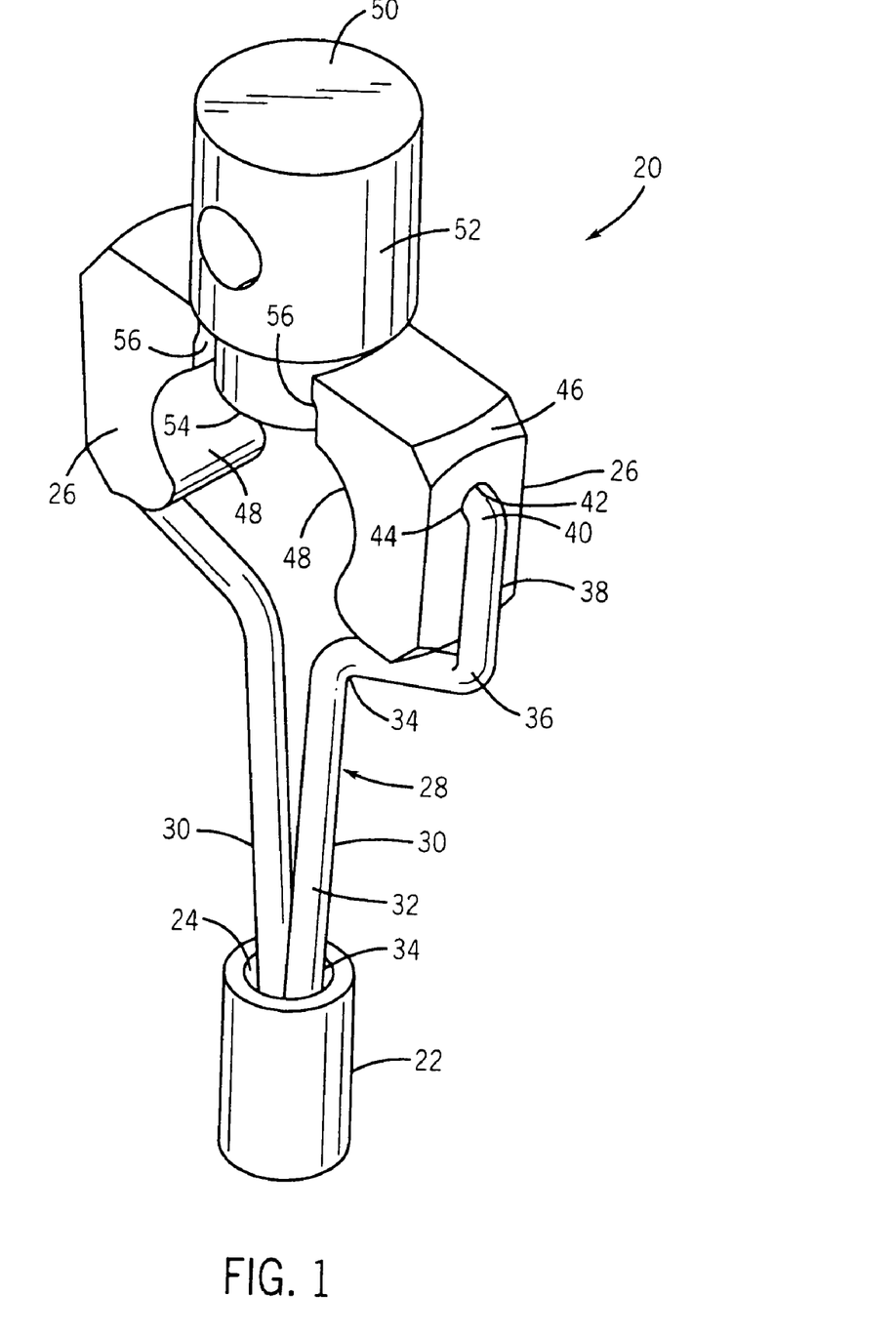
FIG. 1 is a prospective view of a middle ear prosthesis according to a first embodiment of the invention.

Referring to FIG. 1, a middle ear prosthesis 20 according to a first embodiment of the invention is illustrated. In accordance with the invention, the prosthesis 20 comprises a stapes prosthesis having a self-crimping attachment mechanism, as described below.

The prosthesis 20 includes a cylindrical piston 22 having an upwardly opening counter bore 24. The piston 20 is adapted to extend through an oval window when implanted in a human ear. A pair of jaws 26 are provided for engaging an ossicle when implanted in a human ear. A spring 28 is coupled to the jaws 26 for biasing the jaws 26 toward one another to provide clamping pressure.

The piston 22 is generally cylindrical and formed of a biocompatible material, such as titanium or polytetrafluoroethylene (PTFE). The spring 28 comprises a pair of support arms 30. The support arms 30 are identical in construction. The support arms 30 are formed of a biocompatible material and preferably are of a metal wire material having a high spring constant, such as titanium or stainless steel. Each support arm 30 includes an elongate leg 32 having a first end 34 received in the piston counter bore 24. Just above a mid point thereof, the support arm 30 is double reverse bent at 34 and 36 to provide an upper arm 38 generally parallel with the leg 32. The upper arm 38 is turned inwardly at 40 to define an upper end 42 received in an opening 44 in an associated one of the jaws 26.

The support arms 30 are rigidly secured to the piston 22 via a press fit in the counter bore 24 or using an adhesive. As such, the support arms 30, in addition to defining a spring for biasing the jaws toward one another, also operatively connect the jaws 26 to the piston 22.

Each jaw 26 comprises a body 46 of a bioactive material, such as hydroxylapatite. The body 46 includes a semi-cylindrical inner surface 48. The semi-cylindrical inner surface 48 is on an opposite side of the body 46 from the opening 44. As will be appreciated, the shape of the body 46 can take many known forms. However, with the embodiment of FIG. 1, the body 46 includes the opening 44 and semi-cylindrical surface 48, as described.

The semi-cylindrical surface 48 of the pair of jaws 46 face one another. The flexible support arms 30 bias the jaws 26 toward one another to provide clamping pressure, in use, on an anchoring ossicle. To aid in implantation, the prosthesis 20 includes a spacer 50 to temporarily hold the jaws 26 in an open position until implanting in a human ear is completed. The spacer 50 comprises a cylindrical body 52 having a smaller cylindrical end 54. The smaller cylindrical end 54 is received between an upper arcuate edge 56 of the pair jaws 26. The size of the smaller cylindrical portion 54 is greater than the shelf state spacing of the jaws 26 provided by the spring 28 to place the jaws in an open position, as illustrated in FIG. 1. As such, when the spacer 50 is removed, the spring 28 causes the jaws 26 to move toward one another.

In accordance with the invention, the support arm upper ends 42 being received in the jaw openings 44 provides a swivel joint. This provides for an optimal connection to the anchoring ossicle regardless of prosthesis angulation. Additionally, a silicon elastomer may be placed around the support arm upper end 42 at the opening 44 to provide stability.

Figure 2:
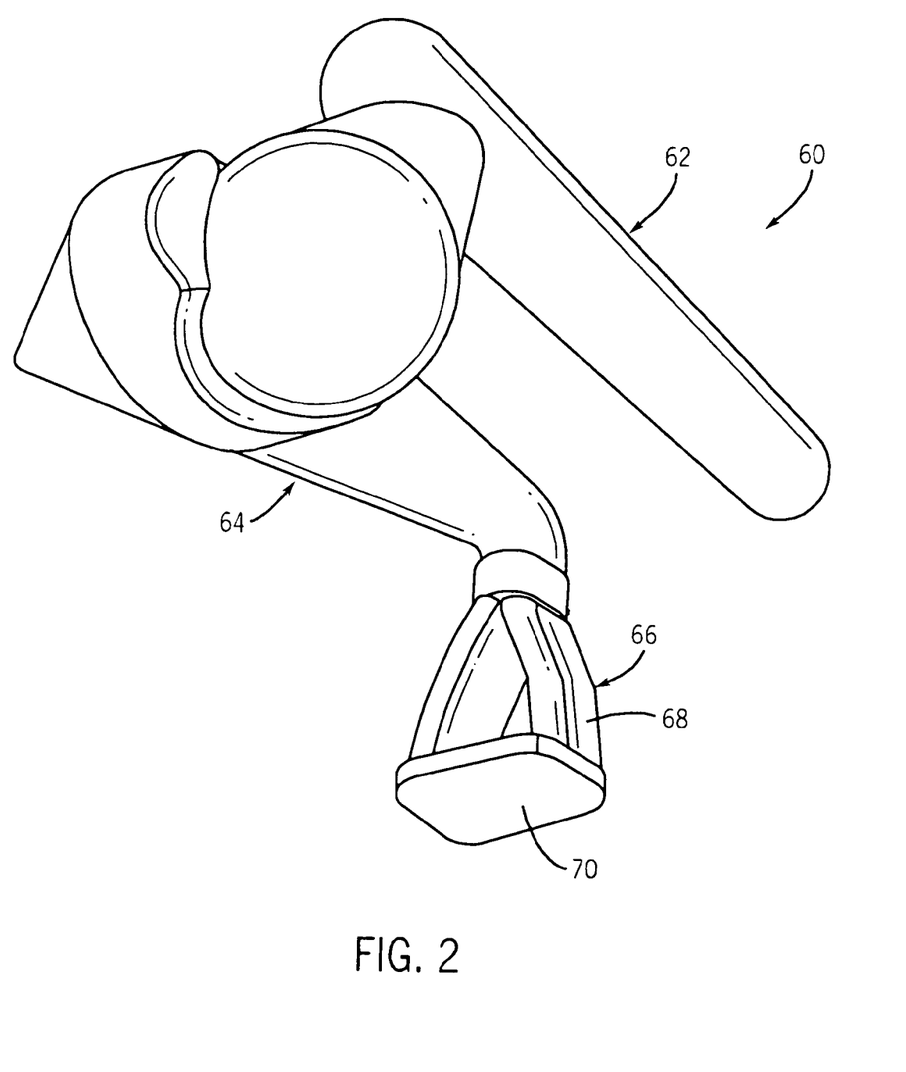
FIGS. 2–6 comprise a series of perspective views illustrating implantation of the prosthesis of FIG. 1 into the middle ear.
Figure 3:
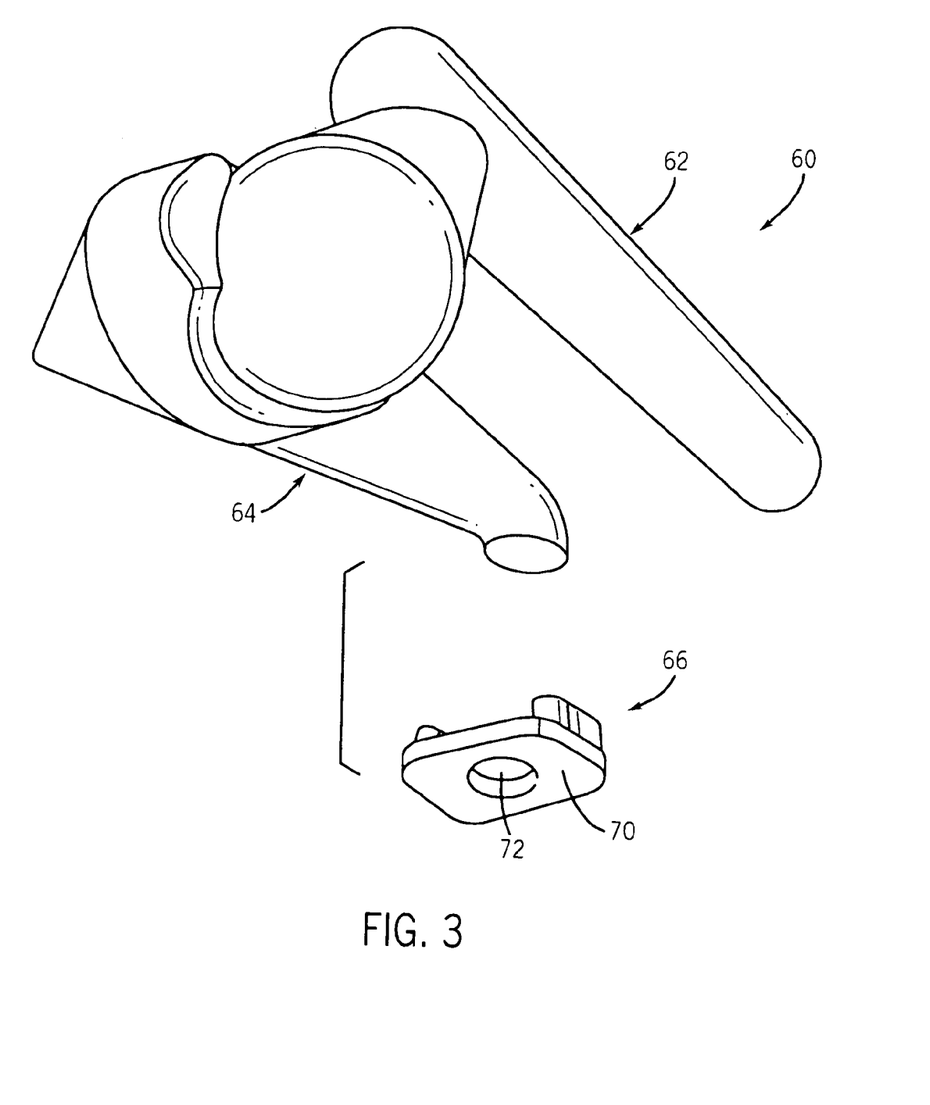
Figure 4:
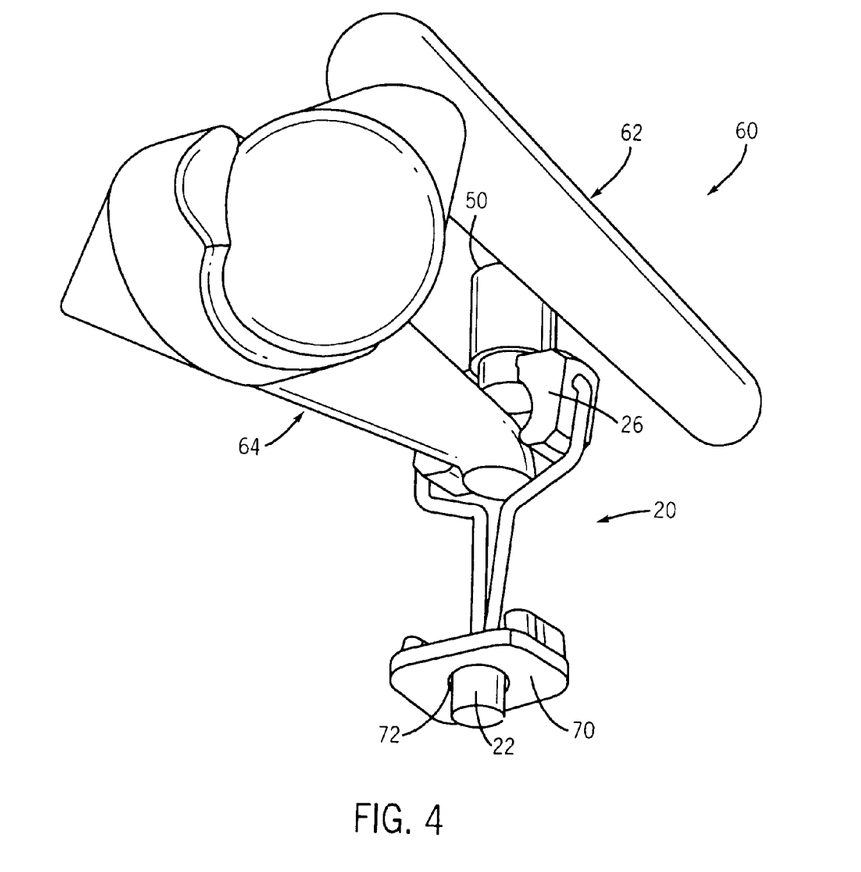

Referring now to FIGS. 2–6, the procedure for implanting the prosthesis 20 of FIG. 1 is illustrated. Referring initially to FIG. 2, the ossicular chain 60 of a human middle ear is illustrated. The ossicular chain includes a malleus 62, an incus 64 and a stapes 66. The stapes 66 includes a loop or arch 68 and a foot plate 70. The foot plate 70 is attached to the oval window of the inner ear, as described above. Referring to FIG. 3, prior to implantation the stapes arch is removed. Additionally, a hole 72 is drilled in the foot plate of the stapes. The hole 72 provides access to the oval window as is well known. Next, and referring to FIG. 4, the stapes prosthesis 20 of FIG. 1 is placed in position with the piston 22 received in the newly created opening 72 in the foot plate 70 to extend through the oval window. The open jaws 26 are positioned on either side of the incus 64. As will be appreciated, the jaws 26 could also be placed around the malleus 62 if the incus 64 is damaged.

Figure 5:
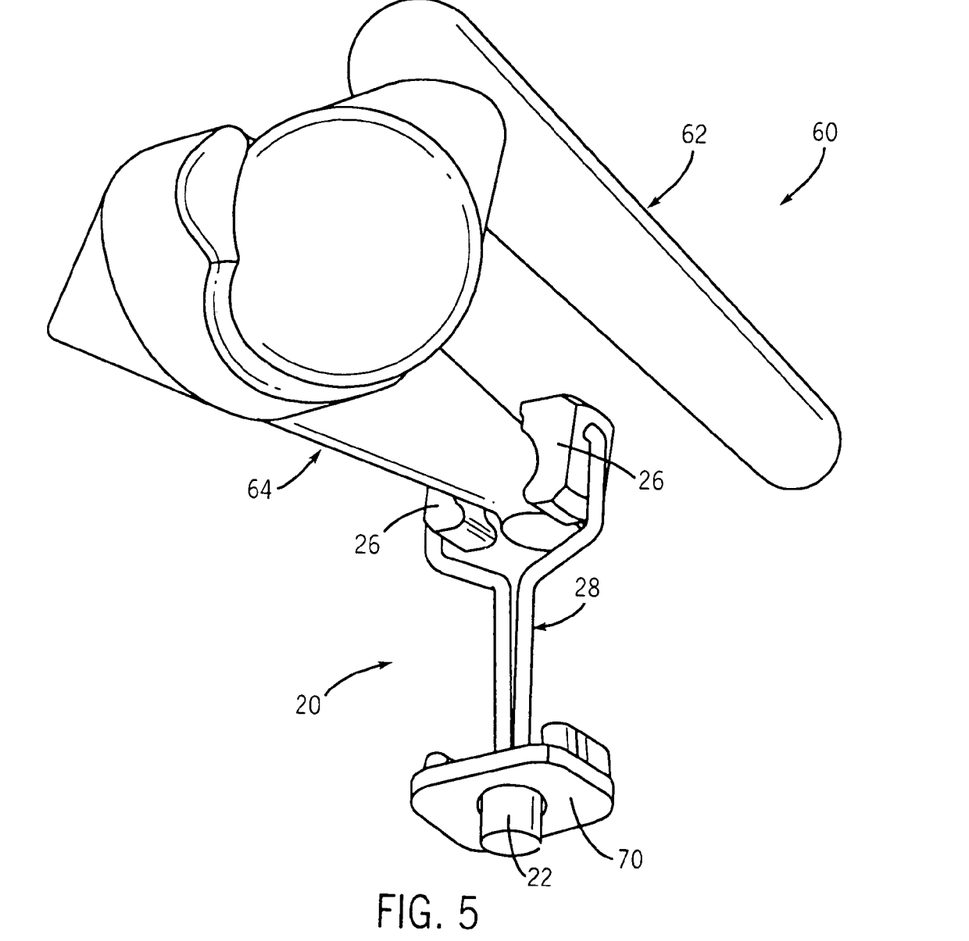
Figure 6:
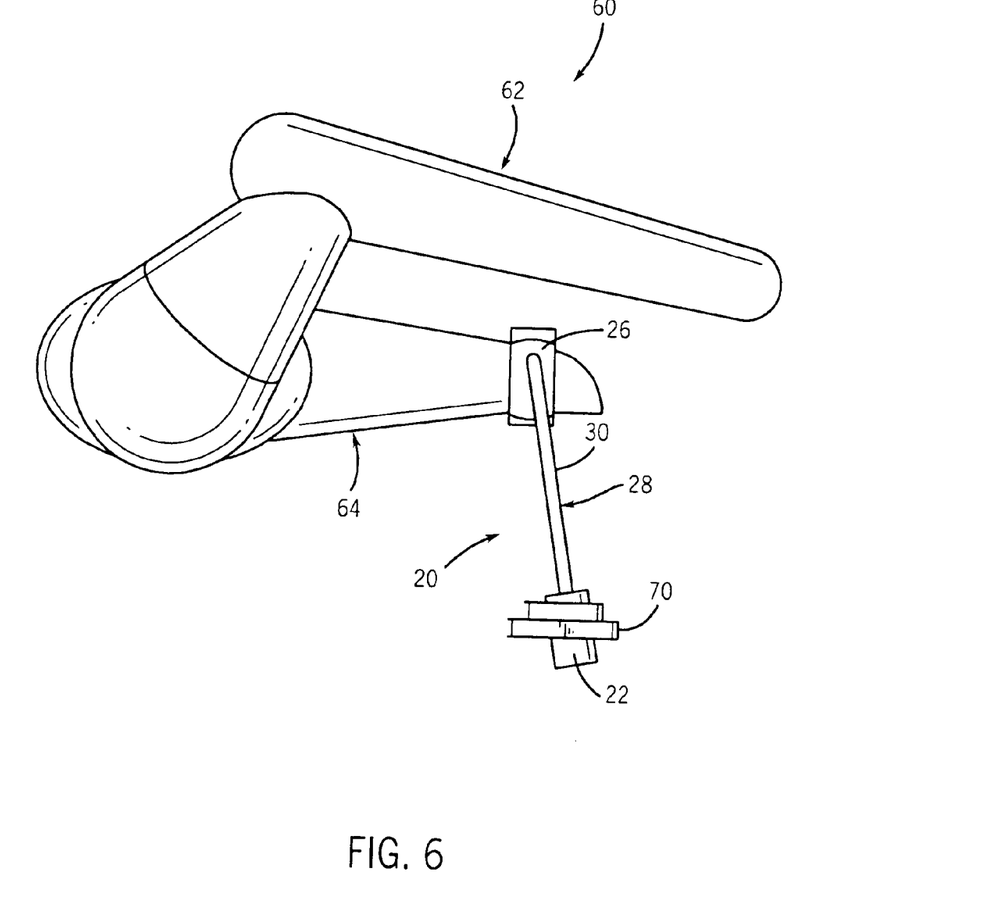

Referring to FIG. 5, the spacer 50 is removed from between the jaws 26. The spring 28 biases the jaws 26 toward one another to provide clamping pressure on the incus 64. FIG. 6 depicts a side view of the ossicular chain 60 with the prosthesis 20 illustrating how the jaws 26 swivel about the support arms 30 to accommodate and adapt to the incus 64. This is evidenced by the angular relationship between the jaws 26 and the support arms 30 and also angular position of the piston 22 in the foot plate 70.

Owing to the described attachment mechanism, the prosthesis 20 may be positioned correctly in the oval window and on the anchoring ossicles prior to engaging the self-crimping jaws 26. The self-retaining mechanism, consisting of the jaws 26 and spring 28, simplifies the insertion of the prosthesis 20 in that the surgeon does not have to crimp or bend the attachment mechanism to provide a secure attachment. The anchoring mechanism may swivel providing an optimal connection to the anchoring ossicle regardless of prosthesis angulation. The prosthesis 20 may be easily removed if revision is necessary. No external energy source, such as a laser, or the like, is required to close the prosthesis. The prosthesis 20 is made from biocompatible and/or bioactive materials.

Figure 7:
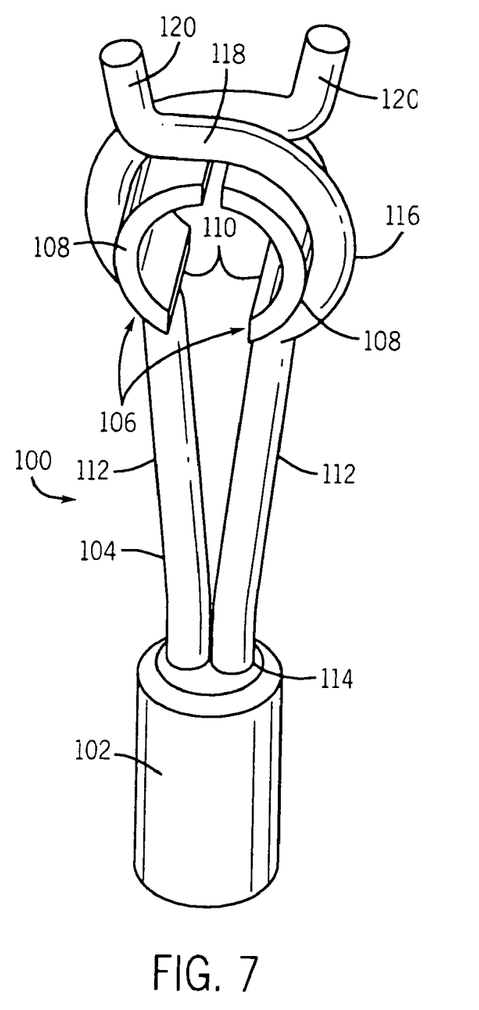
FIG. 7 is a perspective view of a middle ear prosthesis according to a second embodiment of the invention.

Referring to FIG. 7, a middle ear prosthesis 100 according to a second embodiment of the invention is illustrated. The middle ear prosthesis 100 includes a piston 102, a spring 104 and a pair of jaws 106. These elements may be formed of similar materials as with the embodiment of FIG. 1. The jaws 106 comprise semi-cylindrical bodies 108 each defining a semi-cylindrical inner surface 110. The spring 104 comprises a pair of wire support arms 112 each having a lower end 114 attached to the piston 102. Just above a mid point of the support arm 112, the wire is bent to form an arcuate portion 116. The arcuate portion 116 has a similar radius to the jaw cylindrical body 108 and is secured thereto using an adhesive or the like. The wire includes an upper tangential portion 118 extending from the arcuate portion 116 and is turned upwardly at an upper end 120. As is apparent, the two support arms 112 are offset from one another where each is connected to its associated jaw 106 so that the tangential portions 118 overlap and the upper ends 120 are spaced from one another.

Figure 8:
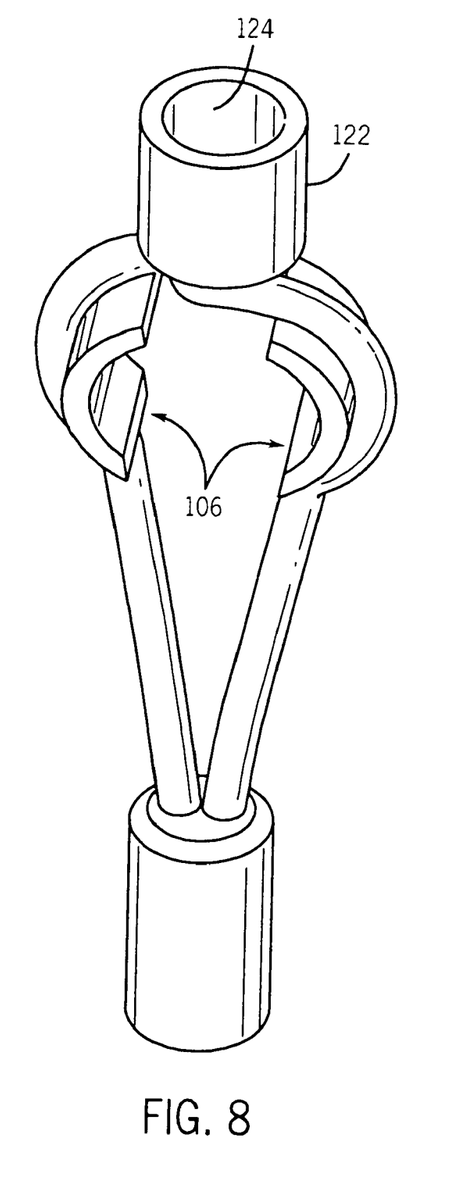
FIG. 8 is a perspective view of the middle ear prosthesis of FIG. 8 shown with a spacer to keep its jaws open.

The prosthesis 100 is illustrated in a closed position in FIG. 7. The jaws 106 are opened by squeezing the upper ends 120 together, as shown in FIG. 8. A tubular spacer 122 having an inner opening 124 smaller than the normal spacing between the spacer upper ends 120 as shown in FIG. 7. The opening 124 is adapted to receive the support arm upper ends 120 when they are squeezed together to maintain the jaws 106 in the open position of FIG. 8 prior to and during implantation.

The procedure for implanting the prosthesis 100 of FIG. 7 is similar to that described relative to FIGS. 2–5.

Figures 9, 10:
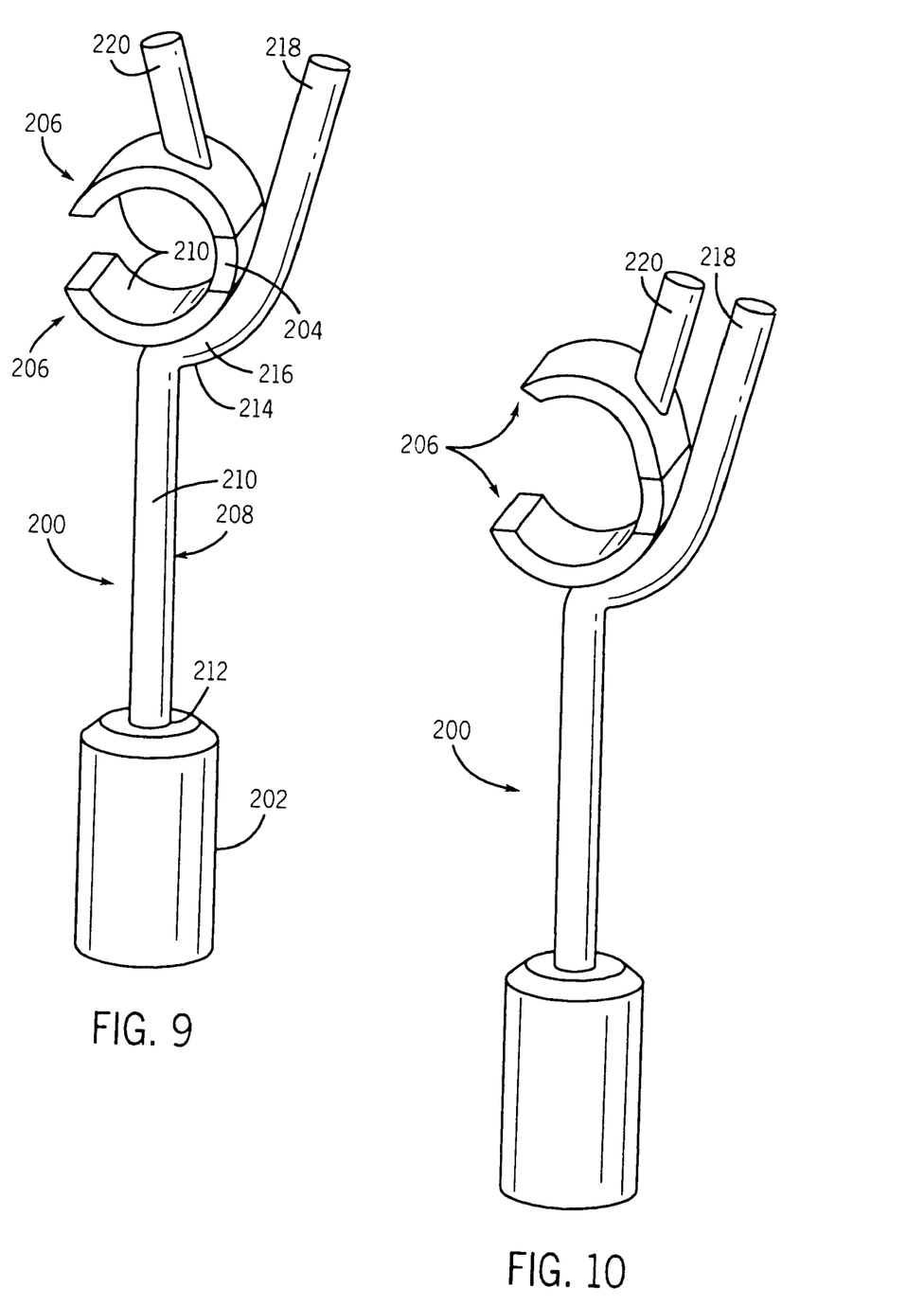
FIG. 9 is a perspective view of a middle ear prosthesis according to a third embodiment of the invention.
FIG. 10 is a perspective view of the middle ear prosthesis of FIG. 9 shown with its jaws in an open position.

Referring to FIGS. 9 and 10, a middle ear prosthesis 200 according to a third embodiment of the invention is illustrated. The prosthesis 200 includes a piston 202, a spring 204, a pair of jaws 206 and a support arm 208 operatively coupled to one of the jaws 206 and the piston 202.

The piston 202 is similar to the piston 22, discussed above. The jaws 206 are generally similar to the jaws 106, see FIG. 7. In the third embodiment, the spring 204 comprises a flexible, spring-like coupling to connect the jaws 206. Particularly, the spring 204 may be of a silicon or pliable plastic that integrally secures the pair of jaws 206 while biasing the jaws 206 toward one another to provide clamping pressure. The jaws 206 are spaced apart so that semi-cylindrical inner surfaces 210 face one another, as shown. The spring element 204 is connected between the jaws 206 to define a substantial "C" shaped attachment mechanism. The material of the spring 204 is different from the material of jaws 206.

The support arm 208 consists of a wire 210 of a biocompatible material, such as the support arms 30 and 112 discussed above, having a lower end 212 attached to the piston 202. The wire is turned above a central portion at 214 to provide an arcuate portion 216 ending in a tangential upper end 218. The tangential portion 216 is attached to a lower one of the two jaws 206 using an adhesive or the like. A short wire 220, of a material similar to the wire 210, is attached to and extends upwardly from the uppermost one of the jaws 206, spaced from the support wire upper end 218.

FIG. 9 illustrates the prosthesis 200 with the jaws 206 in a closed position. The jaws 206 are moved to an open position by squeezing the short wire 220 and long wire upper end 218 together, as shown in FIG. 10. The jaws 206 may be held open by placing a suitable material around the wires 218 and 220 to hold them in position until implantation is complete. Such a material may be similar to the spacer 122 of FIG. 8. The procedure for implanting the prosthesis 200 is similar to that discussed above relative to FIGS. 2–5.

Figure 11:
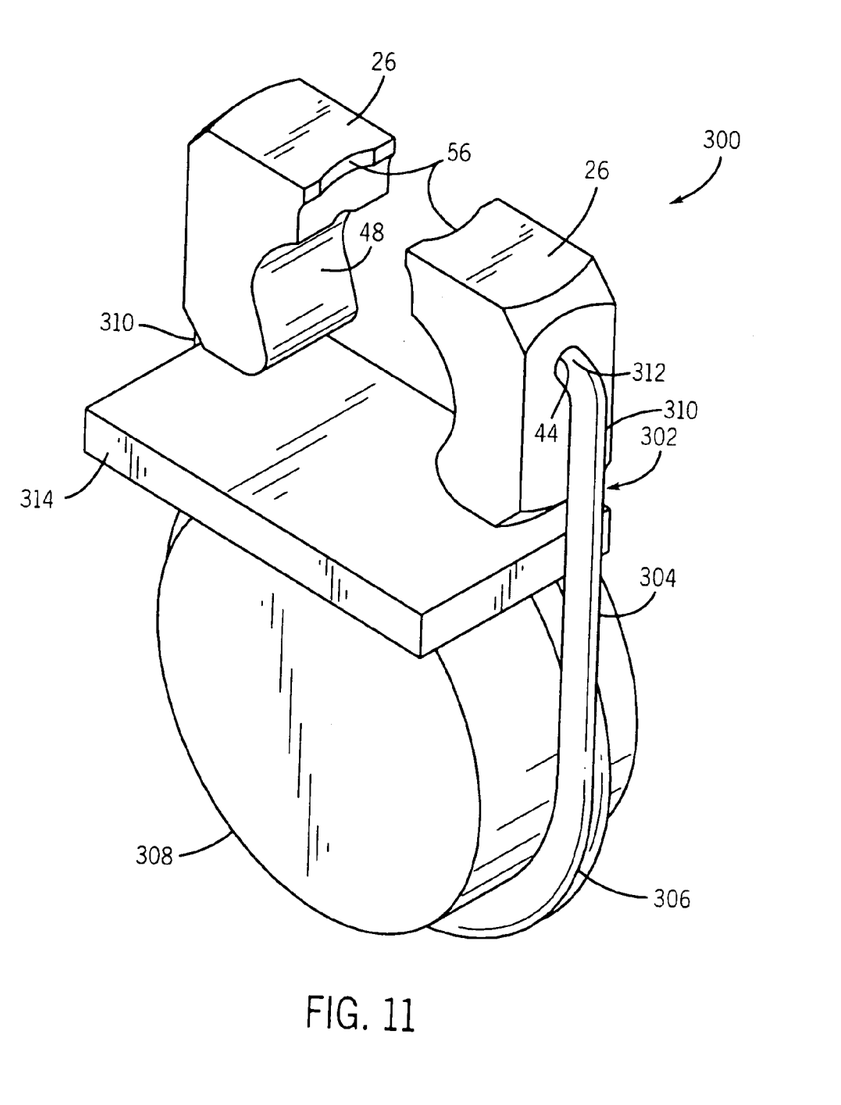
FIG. 11 is a perspective view of a middle ear prosthesis according to a fourth embodiment of the invention.

Referring to FIG. 11, a middle ear prosthesis 300 according to a fourth embodiment of the invention is illustrated. The prosthesis 300 is intended to be an implantable hearing device including an attachment mechanism similar to that with the embodiment of FIG. 1.

The prosthesis 300 includes jaws 26, discussed above relative to FIG. 1. A spring element 302 of a flexible wire material is operatively coupled to the jaws 26 for biasing the jaws toward one another to provide clamping pressure. Particularly, the spring 302 consists of a wire 304 of a biocompatible material, preferably metal, having a high spring constant, such as titanium or stainless steel. The wire 304 is formed in a loop 306 extending around a transducer element 308. Opposite ends of the loop wire 304 comprise support arms 310 having inwardly turned upper ends 310 received in the jaw opening 44 to provide a swivel joint. As above, a silicon elastomer can be placed around the wire upper end 310 and around the opening 44 to provide stability. A spacer element 314 can be placed between the support arms 310 prior to implantation to maintain the jaws 26 in an open position. When the jaws 26 are placed about an ossicle as discussed above, the spacer 314 is removed so that the spring 302 provides clamping pressure to maintain the jaws 26 engaging opposite sides of an ossicle.

The transducer element 308 forms part of an implantable hearing device to transmit force to an ossicle to aid in hearing. The transducer element 308 may be a coil, a magnetic or a piezoelectric element. For example, if the transducer element 308 is a coil, it would be associated with a magnet of the implantable hearing device. If the transducer element 308 is in the form of a magnet, then it would likewise be associated with a coil of an implantable hearing device.

Thus, in accordance with the invention, a self-crimping ossicular prosthesis is illustrated having an improve attachment mechanism in addition to other features.

We claim:

1. A middle ear prosthesis comprising:
   a piston adapted to extend through an oval window when implanted in a human ear;
   a pair of jaws for engaging an ossicle when implanted in a human ear;
   a spring coupled to the jaws for biasing the jaws toward one another to provide clamping pressure, wherein the spring is integrally formed between the pair of jaws and is of a flexible material different from a material of the jaws; and
   means for operatively connecting the jaws to the piston comprising a wire operatively connected to one of the jaws and to the piston.

2. The middle ear prosthesis of claim 1 wherein each of the jaws comprises a body having a semi-cylindrical inner surface.

3. The middle ear prosthesis of claim 1 wherein the spring is of silicon.

4. The middle ear prosthesis of claim 1 wherein the spring is of pliable plastic.

5. The middle ear prosthesis of claim 1 wherein the spring is integrally formed between the pair of jaws to define a C-shaped attachment mechanism.

6. The middle ear prosthesis of claim 1 further comprising a second wire connected to the other jaw so that the wires can be squeezed together to open the jaws.

7. The middle ear prosthesis of claim 1 wherein the spring is of a biocompatible material.

8. The middle ear prosthesis of claim 1 wherein the piston is of a biocompatible material.

9. The middle ear prosthesis of claim 1 wherein the piston is of a material selected from titanium or PTFE.

10. The middle ear prosthesis of claim 1 wherein the jaws are of a bioactive material.

11. The middle ear prosthesis of claim 1 wherein the jaws are of hydroxylapatite.

12. A self crimping ossicular prosthesis comprising:
   a piston adapted to extend through an oval window when implanted in a human ear;
   a pair of jaws of a bioactive material each comprising a body having a semi-cylindrical inner surface for engaging opposite sides of an ossicle when implanted in a human ear, to anchor to the ossicle;
   a spring element of a flexible material, different from the pair of jaws, integrally coupled to the jaws for biasing the jaws toward one another to provide clamping pressure; and
   a support arm operatively coupled to one of the jaws and to the piston.

13. The self crimping ossicular prosthesis of claim 12 wherein the jaws are spaced apart with the semi-cylindrical inner surfaces facing one another, and the spring element is connected between the pair of bodies to define a substantially "C" shaped attachment mechanism.

14. The self crimping ossicular prosthesis of claim 12 further comprising a second arm connected to the other jaw so that the arms can be squeezed together to open the jaws.

* * * * *